United States Patent [19]

Esanu

[11] 4,183,926
[45] Jan. 15, 1980

[54] PHENOTHIAZINE DERIVATIVES, THEIR PREPARATION AND THERAPEUTIC USE

[75] Inventor: André Esanu, Paris, France

[73] Assignee: Societe D'Etudes De Produits Chimiques, Paris, France

[21] Appl. No.: 852,575

[22] Filed: Nov. 17, 1977

[30] Foreign Application Priority Data

Dec. 1, 1976 [GB] United Kingdom ............... 50014/76

[51] Int. Cl.² .................... C07D 417/14; A61K 31/44
[52] U.S. Cl. ........................................ 424/247; 544/43
[58] Field of Search ..................... 544/43; 260/297 V; 424/247

[56] References Cited

U.S. PATENT DOCUMENTS

| | | | |
|---|---|---|---|
| 3,590,046 | 6/1971 | Schaeren | 260/297 V |
| 3,780,035 | 12/1973 | Nakanishi et al. | 544/43 |

*Primary Examiner*—John D. Randolph
*Attorney, Agent, or Firm*—Eyre, Mann, Lucas & Just

[57] ABSTRACT

New phenothiazine derivatives having pharmaceutical activity are disclosed. The compounds are of particular interest because of their neuroleptic activity. The compounds are suitably prepared by reacting an N-substituted phenothiazine with an O,O'-isopropylidenyl-2-methyl-3-hydroxy-4-hydroxymethyl-5-(N-piperazinylmethyl)-pyridine.

2 Claims, No Drawings

PHENOTHIAZINE DERIVATIVES, THEIR PREPARATION AND THERAPEUTIC USE

This invention relates to new phenothiazine derivatives, to a process for their manufacture and to compositions containing them. The new derivatives according to this invention are acid addition salts having the general formula:

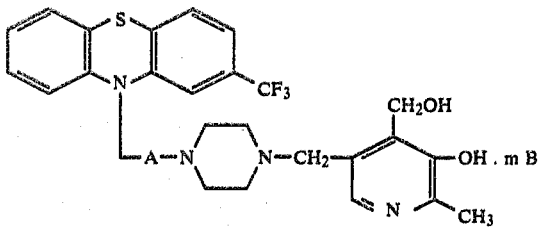

wherein m is an integer from 1 to 3 included, B a therapeutically acceptable acid and A stands for an alkylene chain $C_nH_{2n}$ in which n is an integer from 1 to 5 included.

The compounds of this invention are of particular interest for their neuroleptic action, as shown by various pharmacological experimentations and this invention accordingly provides a therapeutic composition comprising at least one of the compounds according to the above formula in admixture with any therapeutically acceptable diluent or carrier.

The compounds according to this invention may be prepared by the reaction of the appropriate N-substituted phenothiazine of the formula:

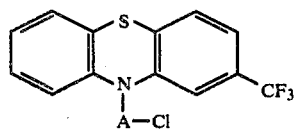

on O,O'-isopropylidenyl-2-methyl-3-hydroxy-4-hydroxymethyl-5-(N-piperazinylmethyl)-pyridine of the formula:

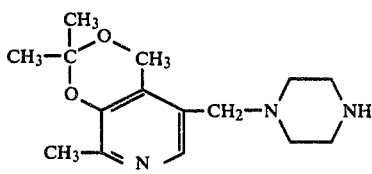

in a solvent such as toluene, in the presence of potassium carbonate and copper, the reaction being performed at the boil for some hours. There is thus obtained the compound:

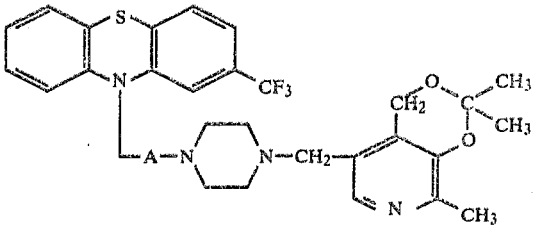

which is transformed in one compound according to the invention by treatment at a temperature from room temperature to about 90° C. by the selected acid B; this treatment results simultaneously in the breaking of the isopropylidene bridge and in the salification.

The substituted N-phenothiazine mentioned above may be prepared by reacting phenothiazine on sodium metal in liquid ammonia and treating the compound thus obtained by the dihalide Cl-A-Br. The O,O'-isopropylidenyl-2-methyl-3-hydroxy-4-hydroxymethyl-5-(N-piperazinylmethyl)-pyridine may be prepared as indicated in our previous U.S. Pat. No. 3,903,088.

The following examples illustrate this invention:

EXAMPLE 1

γ-[N-(2-methyl-3-hydroxy-4-hydroxymethyl-5-pyridylmethyl-N'-piperazinyl]-10-propyl-2-trifluoromethyl-phenothiazine hydrochloride Into a 5 liter reactor fitted with stirring and cooling means and maintained at about −40° C., there were poured 1 liter of liquid ammonia, 11.5 g (0.5 mole) of metallic sodium, 0.5 g of ferric acetate and then, slowly, 133.5 g (0.5 mole) of 2-trifluoromethyl-phenothiazine. The mixture was stirred for one hour and there were added 78.8 g (0.5 mole) of 1-bromo-3-chloropropane. After stirring for some minutes, the mixture was allowed to warm slowly up to room temperature, with elimination of the liquid ammonia. There were then added 2 liters of heptane and stirring was maintained for 12 hours. The mixture was then refluxed for one hour and filtered, washed with heptane, evaporated to dryness and recrystallized from heptane to give 270 g (yield 81%) of N-(γ-chloropropyl)-2-trifluoromethyl-phenothiazine.

100 g (0.3 mole) of this product were placed in a 2 liter reactor with 110.6 g (0.4 mole) of O,O'-isopropylidenyl-2-methyl-3-hydroxy-4-hydroxymethyl-5-(N-piperazinylmethyl)-pyridine, 55.2 g (0.4 mole) of dry potassium carbonate, 1 g of copper powder and 0.75 liter of dried toluene.

The mixture was refluxed for 14 hours and there was added 0.25 liter of methyl isobutyl ketone. The mixture was then once more refluxed for 4 hours and evaporated to dryness.

The dried product was dissolved in petroleum ether then in iced isopentane which was evaporated to provide 160 g of an oily product which was hydrolyzed by formic acid in aqueous ethanol to break the isopropylidene bridge across the 3- and 4-substituents of the pyridoxine nucleus. The resulting product was treated with an ammonia solution, extracted with chloroform, then acidified with hydrochloric acid. After crystallization from ethanol/methanol (50/50) there were finally obtained 161 g of a pale yellow powder melting at 203° C., soluble in water and dimethylsulphoxide, and insoluble in ethanol and chloroform. Analysis of the product showed a good correspondence with the formula $C_{28}H_{31}O_2N_4S\ F_3,\ 3\ HCl$.

EXAMPLE 2

γ-[N-methyl-3-hydroxy-4-hydroxymethyl-5-pyridyl-methyl-N'-piperazinyl]-10-butyl-2-trifluoromethyl-phenothiazine hydrochloride This compound was prepared as described in example 1 but 1-bromo 3-chloropropane was replaced by 1-bromo 4-chlorobutane; yield was 63% in a yellow product, the analysis of which shows a good correspondence with the formula $C_{29}H_{32}O_2N_4S\ F_3,\ 2\ HCl$.

TOXICITY

The toxicity has been determined on mice; per os the LD 50 was 750 mg/kg whereas IP, LD 50 was about 250 mg/kg.

By comparison with various other products of similar activity such as chlorpromazine, levomepromazine and haloperidol, the compounds of the invention have a lowest per os toxicity whereas the IP toxicity is equal to the lowest of the 3 other compounds.

PHARMACOLOGY

A. Spontaneous motility on mice

Two batches of each 12 female mice (20–22 g) have received per os 8 or 16 mg/kg of the compound of example 1 and actimetry has been determined according to the J. R. BOISSIER method.

At 8 mg/kg the activity of mice has decreased by 31.5–33% (10 to 15 minutes); at 16 mg/kg the figures were 53–57% in the same conditions.

B. Action on body temperature and ptosis on mice

At the dose of 30 mg/kg, the variation of the temperature of the body and the ptosis were appreciated on female mice. By comparison with control animals, the compound of example 1 gave a lowering of body temperature on female mice of about 3° (minimum lowering at 30' and 7 hours after administration) to a maximum of about 7° at 2 hours. Palpebral ptosis appreciated simultaneously (scale of quotation: (0 to 4) showed the highest figures (4.5) at 1 hour but was quoted 1.5 at 7 hours.

C. Group toxicity with amphetamine

This experimentation has been undertaken on mice comparatively on the compound at example 1 and on chlorpromazine according to the technique described by SIMON P. et CHERMAT (1973) Recherche d'une interaction avec les stéréotypies provoquées par l'amphétamine chez le rat. J. Pharmacol (PARIS) 1973. 3 2. 235–238. Various batches of each 10 female mice (20–22 g) were treated per os by increasing doses of either the tested compound or chlorpromazine; one batch, used as control did not receive any product and all the batches received one hour after 35 mg/kg of amphetamine (Intraperitoneously). The results are summarzied in the following table where the deaths are reported at 3 and 24 hours after injections of amphetamine.

| Product | Dose mg/kg,P.O. | Deaths at: 3 hours | 24 hours | Total | % of protection |
|---|---|---|---|---|---|
| Amphetamine control | | 3 | 4 | 7 | |
| Example 1 compound | 1 | 0 | 6 | 6 | 14 % |
| | 3 | 2 | 1 | 3 | 57 % |
| | 10 | | | 0 | 100 % |
| Chlorpromazine | 1 | 2 | 6 | 8 | 0 % |
| | 3 | 3 | 3 | 6 | 14 % |
| | 10 | | | 0 | 100 % |

This experimentation shows a better result for the compound of the invention with respect to chlorpromazine.

POSOLOGY—PRESENTATION

The compounds according to the invention may be administered under any suitable form, for instance as gelatine capsules containing 25 or 50 mg associated if desired with any suitable carrier. In human therapy 25 to 175 mg may be administered per diem.

I claim:

1. A phenothiazine derivative of the formula:

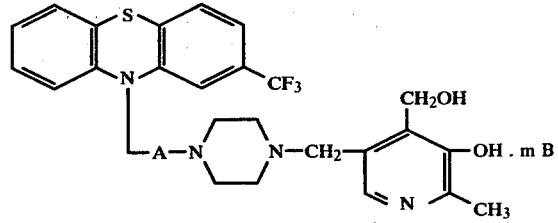

wherein m is an integer from 1 to 3 included, B a therapeutically acceptable acid and A stands for an alkylene chain $C_nH_{2n}$ in which n is an integer from 1 to 5 included.

2. A therapeutic composition for use as a neuroleptic, said composition comprising, in a pharmaceutically effective amount, a compound selected from the group consisting of those compounds of claim 1 and mixtures thereof, in a pharmaceutically acceptable carrier.

* * * * *